US008532395B2

(12) United States Patent
Mitsui

(10) Patent No.: US 8,532,395 B2
(45) Date of Patent: Sep. 10, 2013

(54) PATTERN INSPECTION METHOD AND SEMICONDUCTOR DEVICE MANUFACTURING METHOD

(75) Inventor: Tadashi Mitsui, Kamakura (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 255 days.

(21) Appl. No.: 13/014,171

(22) Filed: Jan. 26, 2011

(65) Prior Publication Data

US 2011/0286658 A1  Nov. 24, 2011

(30) Foreign Application Priority Data

May 24, 2010 (JP) ................................ 2010-118618

(51) Int. Cl.
*G06K 9/48* (2006.01)
(52) U.S. Cl.
USPC ........... 382/199; 382/100; 382/149; 382/190; 348/125; 438/12; 356/394
(58) Field of Classification Search
USPC ................................................. 382/190–199
See application file for complete search history.

(56) References Cited

U.S. PATENT DOCUMENTS

| | | | | |
|---|---|---|---|---|
| 3,983,479 A * | 9/1976 | Lee et al. | | 324/537 |
| 4,718,767 A * | 1/1988 | Hazama | | 356/389 |
| 4,791,586 A * | 12/1988 | Maeda et al. | | 716/112 |
| 6,529,613 B1 * | 3/2003 | Astle | | 382/103 |
| 6,610,550 B1 * | 8/2003 | Pasadyn et al. | | 438/14 |
| 6,640,000 B1 * | 10/2003 | Fey et al. | | 382/128 |
| 6,842,245 B2 * | 1/2005 | Ando | | 356/394 |
| 7,055,127 B2 * | 5/2006 | Pierrat et al. | | 716/53 |
| 7,453,456 B2 * | 11/2008 | Petrov et al. | | 345/419 |
| 7,614,033 B2 * | 11/2009 | Pierrat et al. | | 716/50 |
| 7,619,751 B2 * | 11/2009 | Yamaguchi et al. | | 356/605 |
| 7,702,157 B2 * | 4/2010 | Mitsui | | 382/199 |
| 7,941,767 B2 * | 5/2011 | Mukai et al. | | 716/50 |
| 8,086,041 B2 * | 12/2011 | Mitsui | | 382/199 |
| 8,144,338 B2 * | 3/2012 | Mitsui | | 356/604 |
| 2002/0052053 A1 * | 5/2002 | Ono et al. | | 438/12 |
| 2003/0015660 A1 * | 1/2003 | Shishido et al. | | 250/311 |
| 2003/0142860 A1 * | 7/2003 | Glasser et al. | | 382/144 |
| 2005/0226494 A1 * | 10/2005 | Yamamoto et al. | | 382/149 |
| 2006/0262977 A1 * | 11/2006 | Mitsui | | 382/209 |
| 2007/0051470 A1 * | 3/2007 | Iwakoshi et al. | | 156/345.28 |
| 2007/0098249 A1 * | 5/2007 | Miyano et al. | | 382/145 |

(Continued)

FOREIGN PATENT DOCUMENTS

JP  2002-134577  5/2002
JP  2002134577 A  *  5/2002

*Primary Examiner* — Jayesh A Patel
*Assistant Examiner* — Iman K Kholdebarin
(74) *Attorney, Agent, or Firm* — Finnegan, Henderson, Farabow, Garrett & Dunner, L.L.P.

(57) ABSTRACT

In one embodiment, a pattern inspection method is disclosed. The method can include predicting an edge shape at a given future time with respect to the same inspection target pattern, setting a threshold corresponding to a required specification of the inspection target pattern, and predicting the time when the inspection target pattern fails to meet the required specification from the predicted edge shape and the threshold. The method can further include taking a plurality of images concerning the inspection target pattern at different times by use of an imaging apparatus, detecting edges of the obtained images, respectively, matching the detected edges of different imaging times, and obtaining a difference between corresponding edges to generate a difference vector after the matching. The edge shape of the future time can be predicted based on the generated difference vector and an interval between the imaging times.

15 Claims, 7 Drawing Sheets

(56) References Cited

U.S. PATENT DOCUMENTS

| | | | |
|---|---|---|---|
| 2008/0256504 A1* | 10/2008 | Oishi et al. | 716/19 |
| 2009/0161943 A1* | 6/2009 | Yamashita et al. | 382/149 |
| 2009/0263023 A1* | 10/2009 | Iwamoto | 382/199 |
| 2009/0304261 A1* | 12/2009 | Takahashi et al. | 382/149 |
| 2010/0131915 A1* | 5/2010 | Hirabayashi | 716/21 |
| 2010/0232707 A1* | 9/2010 | Kato et al. | 382/199 |
| 2011/0237087 A1* | 9/2011 | Yoshikawa | 438/795 |
| 2011/0286658 A1* | 11/2011 | Mitsui | 382/149 |
| 2012/0121173 A1* | 5/2012 | Aisaka et al. | 382/165 |

* cited by examiner

PATTERN INSPECTION METHOD AND SEMICONDUCTOR DEVICE MANUFACTURING METHOD

CROSS REFERENCE TO RELATED APPLICATIONS

This application is based upon and claims the benefit of priority from the prior Japanese Patent Application No. 2010-118618, filed on May, 24, 2010, the entire contents of which are incorporated herein by reference.

FIELD

Embodiments described herein relates generally to a pattern inspection method and a semiconductor device manufacturing method.

BACKGROUND

Due to miniaturization of semiconductor devices, a haze (defect) on a reticle generated in a lithographic process has been a major issue. The haze on the reticle is said to be caused when nuclei agglutinate due to exposure energy, the nuclei being formed by a chemical reaction between an acid and a base present in the surface of the reticle or present in atmosphere or formed by a photochemical reaction of organic impurities. The haze on the reticle is increased in size by, e.g., the photochemical reaction whenever exposure is repeated, and finally grows into a size in which the haze may be regarded as a defect on a wafer. Therefore, the haze is called a growing defect (hereinafter briefly referred to as "GD"). Recently, due to the miniaturization of semiconductor devices, resolution has been improved by a reduced wavelength of a light source of an exposure apparatus. Accordingly, light energy provided for the photochemical reaction has been increased, and the growth rate of the defect has been further rising. For example, in exposure using a light source of KrF (wavelength: 248 nm), the GD affects about 5% of the reticle. On the other hand, in exposure using a light source of ArF (wavelength: 193 nm), the GD affects 20% of the whole reticle. This is the cause of a decreased yield.

As countermeasures, ammonium sulfate which is one of the causative substances is removed from the exposure apparatus through a filter in an attempt to inhibit the generation of the GD. However, in the present situation, the generation of the GD is not prevented completely. While the generated GD can be partly removed by cleaning the reticle, this cleaning process not only requires the cleaning of the reticle but also requires the removal of a pellicle and the attachment of a new pellicle after the cleaning. This leads to additional costs. Moreover, if cycles of cleaning the reticle are increased to reduce the GD, a phase shift, reticle transmittance and a mask CD value change whenever cleaning is repeated. Disadvantageously, this results in a reduced life of the reticle and a significant rise in costs. Therefore, at the present time, the generated GD has to be detected before a device yield is severely affected. As a result, the reticle has to be frequently inspected, leading to a problem of decreased productivity.

As is already known, not all the defects detected on the reticle are transferred onto the wafer and form defects. For example, in the manufacture of a semiconductor device, defects transferred onto the wafer are only regarded as important. Accordingly, one method to enable an inspection that takes into account the defect transferring tendency of the reticle is to simulate an exposure optical system by a computer, thereby to create actual wafer images with respect to images of transmitted light and reflected light of the reticle, and to detect defects in the wafer images. However, a unit that carries out this method has to be provided with an optical system equivalent to that of the exposure apparatus and thus leads to a higher hardware price. Consequently, there is a problem of significantly increased inspection costs in the case of frequent inspections for monitoring the growth of a defect such as the GD. Furthermore, a current GD inspection is intended to detect defects generated on an L/S (Line and Space) pattern, and therefore uses, for example, an inspection specification stipulating that a representative CD value of a defect be 10% or less of a design CD. However, in the case of a GD generated on a complex pattern shape of, for example, a peripheral portion, it is difficult to define a representative CD value, and the above-mentioned inspection specification is meaningless.

DETAILED DESCRIPTION

In one embodiment, a pattern inspection method is disclosed. The method can comprise predicting an edge shape at an arbitrary future time with respect to the same inspection target pattern, setting a threshold corresponding to a required specification of the inspection target pattern, and predicting the time when the inspection target pattern fails to meet the required specification from the predicted edge shape and the threshold. The method can further comprise taking a plurality of images concerning the inspection target pattern at different times by use of an imaging apparatus, detecting edges of the obtained images, respectively, matching the detected edges of different imaging times, and obtaining a difference between corresponding edges to generate a difference vector after the matching. The edge shape of the future time can be predicted based on the generated difference vector and an interval between the imaging times.

Embodiments will now be explained with reference to the accompanying drawings. Like numbers are assigned to like parts throughout the drawings, and repeated explanations are given only when necessary. Although a GD generated in a photolithographic mask in a semiconductor device manufacturing process is evaluated in the case described below by way of example, changes of a pattern made with time in other semiconductor device manufacturing processes such as a wet treatment, etching and film formation may be evaluated in other applicable embodiments. The embodiments mentioned below can also be applied to processes of manufacturing products other than a semiconductor device, such as a flat panel display or printed board.

Figure 1:
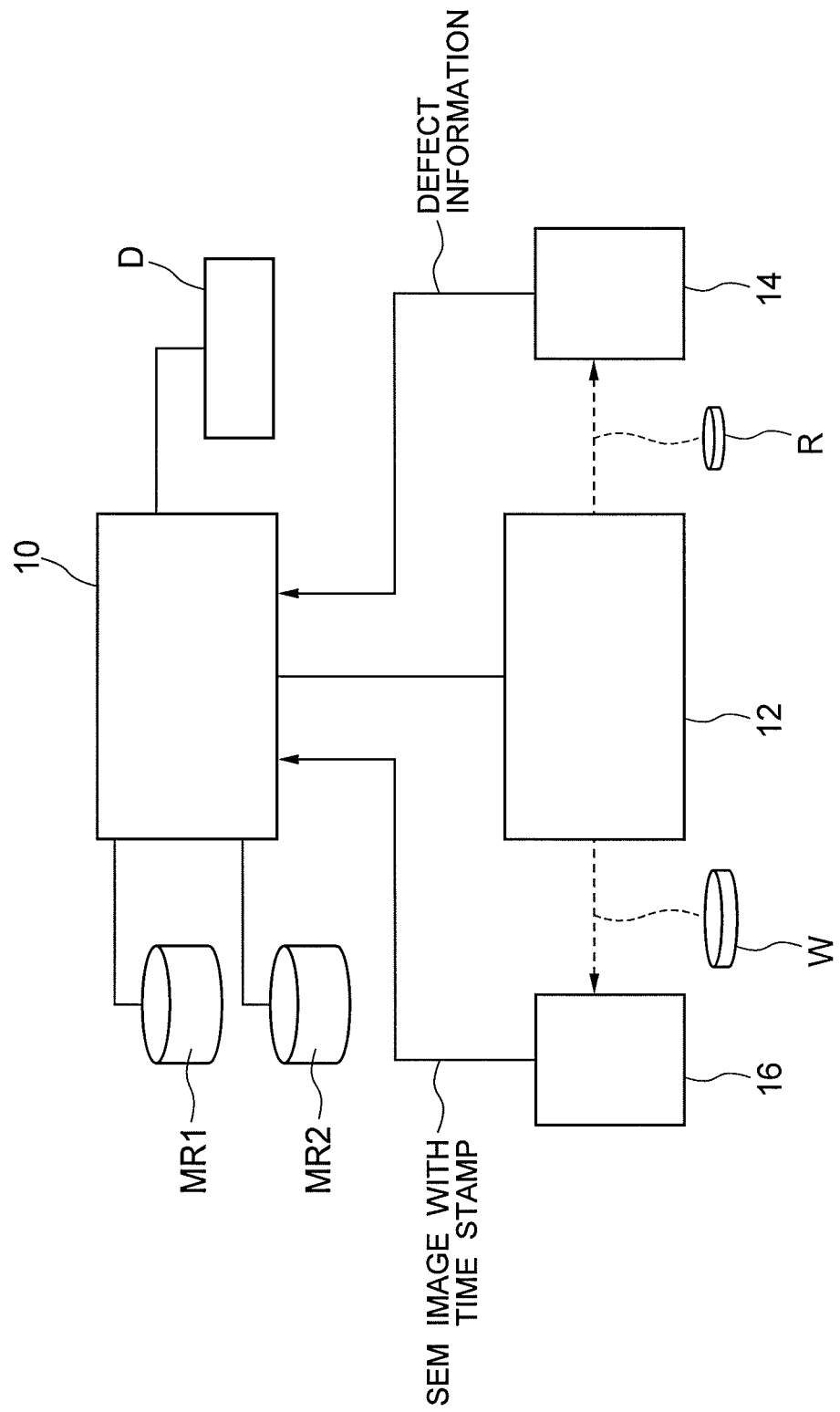
FIG. 1 is a block diagram showing a semiconductor manufacturing unit including a pattern inspection apparatus according to one embodiment.

FIG. 1 is a block diagram showing a semiconductor manufacturing unit including a pattern inspection apparatus 10 for carrying out a pattern inspection according to the embodiment. In addition to the pattern inspection apparatus 10, the semiconductor manufacturing unit in FIG. 1 includes a pattern forming apparatus 12, a reticle defect defecting apparatus 14 and a critical dimension-scanning electron microscope (CD-SEM) apparatus 16.

The pattern forming apparatus 12 performs a series of processing for pattern formation: pattern exposure processing for applying an energy ray to a reticle R in which a reticle pattern as an inspection target pattern is formed and thus transferring the reticle pattern onto a wafer W; a wet treatment for, for example, etching a resist; and cleaning processing for getting rid of materials removed by the etching. The CD-SEM apparatus 16 images the pattern formed on the Si wafer W by the pattern forming apparatus 12, and supplies the pattern inspection apparatus 10 with information on the SEM image together with a time stamp indicating the imaging date and time. The reticle defect defecting apparatus 14 detects a defect on the reticle R used by the pattern forming apparatus 12, and then supplies the detection result to the pattern inspection apparatus 10. The reticle defect defecting apparatus 14 uses an optical inspection method and therefore does not have a high detection sensitivity as compared to, for example, an SEM apparatus, but is capable of inspecting the entire surface of the reticle faster than the SEM apparatus.

A display D and an external hard disc drives MR1 and MR2 are connected to the pattern inspection apparatus 10. A recipe file containing a specific procedure of steps of the pattern inspection described below in detail is stored in the external hard disc drive MR1. The pattern inspection apparatus 10 reads the recipe file from the hard disc drive MR1 to carry out a pattern inspection, and displays an inspection result on the display D. The inspection result includes later-described information for prompting to clean or replace the reticle. A storage medium is not limited to a fixed storage medium such as the hard disc drives MR1 and MR2 or a memory, and may be a portable storage medium such as a magnetic disk or optical disk.

Figure 2:
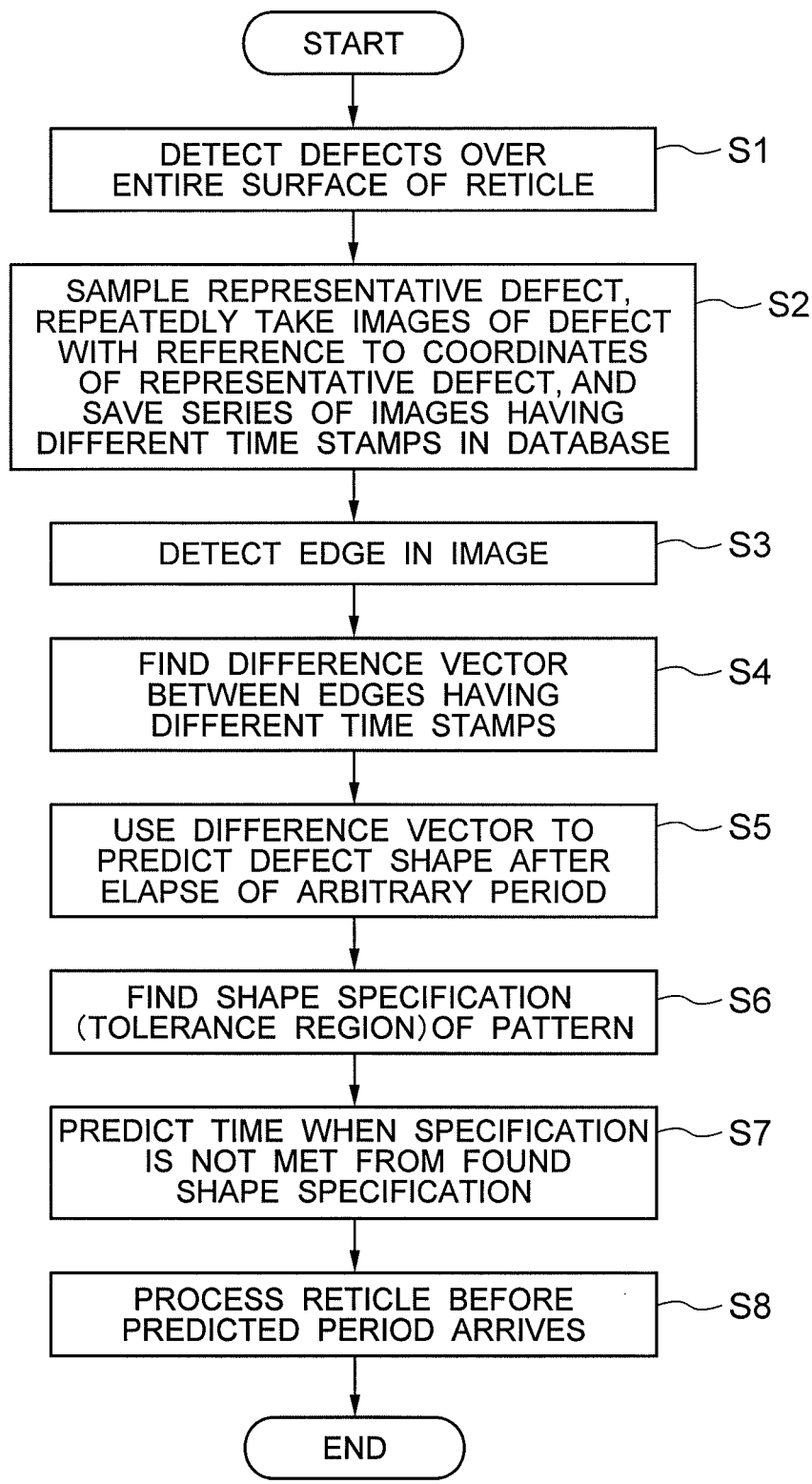
FIG. 2 is a flowchart illustrating an outline process according to an embodiment.

FIG. 2 is a flowchart showing an outline of the pattern inspection according to the embodiment. The outline process in FIG. 2 is briefly described first, and its detailed contents process will be described later.

First, defects on the reticle R are detected by the reticle defect defecting apparatus 14 (step S1).

Then, a representative defect is sampled from among the detected defects. Referring to coordinates of this defect, the Si wafer W, in which a pattern including the defects is formed, is imaged by the CD-SEM apparatus 16, and this image is supplied to the pattern inspection apparatus 10 together with a time stamp. Further, images of the same defect are repeatedly taken and supplied to the pattern inspection apparatus 10 whenever an arbitrary period elapses. As a result, a series of defect images having different time stamps are stored in the external hard disc drive MR2 as an image database (step S2).

Then, edges are detected from the series of defect images acquired (step S3), and a difference vector is obtained between the edges having different time stamps out of the detected edges (step S4). Here, the difference vector is a concept that is commonly used, for example, in an encoding apparatus and encoding method and in a decoding apparatus and decoding method. In general, for example, in a vision system, the motion of an object such as a human being or vehicle is efficiently expressed in the form of vector data such as a motion vector. A subtraction of one of two motion vectors from the other is often defined as the motion vector. Thus, difference data is smaller in amount than simple difference data obtained with the vector data being neglected, so that, for example, the compression ratio of a moving image can be higher.

Then, the obtained difference vector is used to predict the future shape of the defect which would appear after elapse of an arbitrary period (step S5).

Then, a shape specification (tolerance region) of the inspection target pattern is found (step S6) as a reference for judging whether the obtained prediction shape of the defect affects yield. From the found shape specification, the time when the specification is not met is predicted (step S7). Finally, the reticle is cleaned and replaced before the predicted period arrives (step S8).

The steps described above are explained in more detail below with reference to FIG. 3 to FIG. 15.

(Process in step S1)

As described above, not all the defects detected in the entire surface of the reticle R are GDs. If defects that do not meet the specification are detected at this stage, some measures are taken to clean or discard the reticle R. Although a defect is detected in the first inspection in the present embodiment, this is based on a generally conceivable assumption that the size of the defect still meets the specification. In this case, measures have to be taken to, for example, clean the mask immediately before GDs among the defected defects affect the yield of the device through the growth process of the GDs. Therefore, the growth process of the defected defect has to be continuously monitored.

(Process in Step S2)

Here, ten defects are sampled by way of example. In order to sample the defects, the defects may be selected in descending order of size by an optical inspection, or may be selected in descending order of the risk of the places where defects are generated, or may be selected by weighting in which the above-mentioned two factors are taken into account. An SEM image corresponding to coordinates of the selected ten defects is stored in the external memory MR2. The SEM image database not only stores the taken images but also stores the coordinates of the imaged defects and imaging dates and times in the form of time stamps. Such time-series defect images are to be evaluated. However, in the following case, for the simplicity of explanation, 100 first defect images ImgA and 100 images ImgB taken one week after the date on which the images ImgA are taken are stored.

Figure 3:
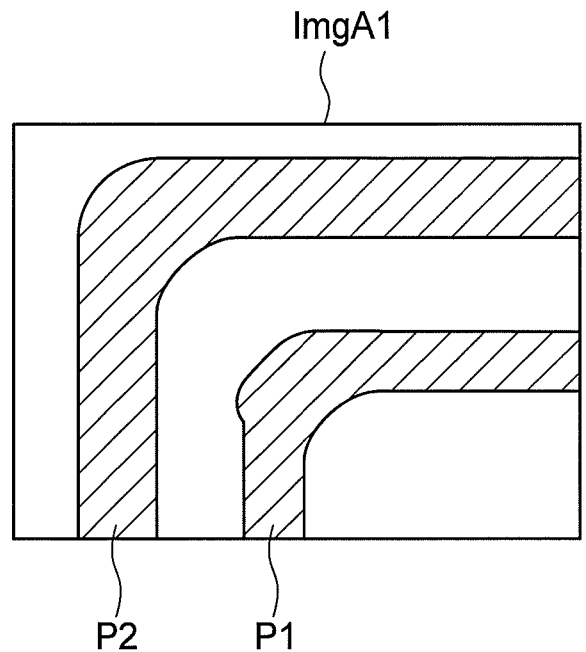
FIG. 3 is an explanatory diagram of step S3 in FIG. 2.
Figure 4:
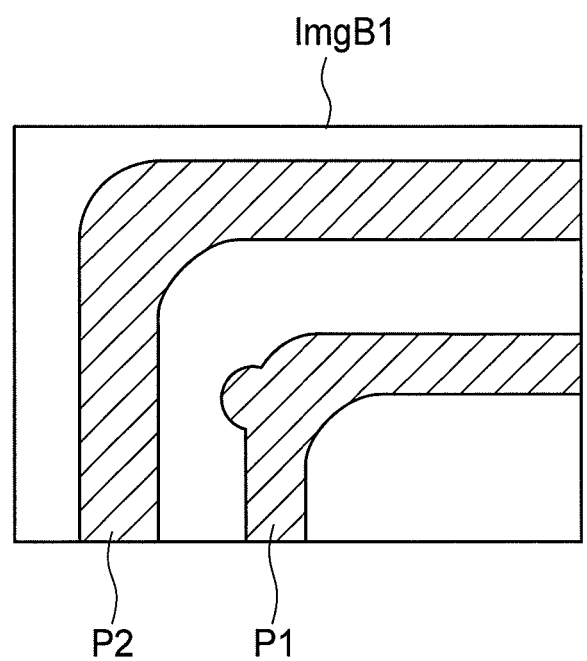
FIG. 4 is an explanatory diagram of steps S3 and S4 in FIG. 2.
Figure 5:
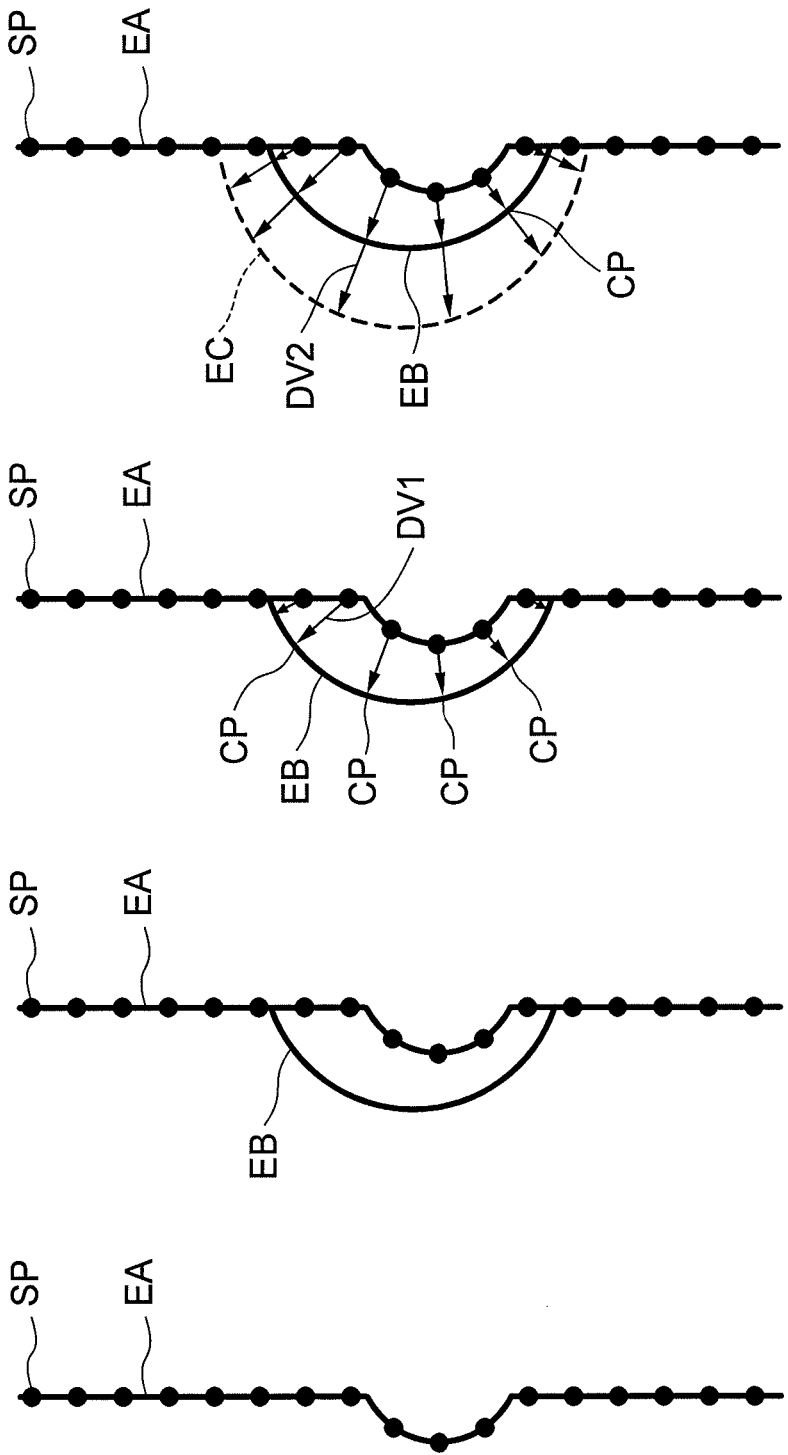
FIG. 5A to FIG. 5D are explanatory diagrams showing how to take corresponding points.

One example of the first defect image ImgA is shown by ImgA1 in FIG. 3, and the defect image ImgB taken one week after the imaging date of the ImgA1 is shown by ImgB1 in FIG. 4. These diagrams are enlarged views of highly risky portions of two two-dimensional patterns P1 and P2.

(Process in Step S3)

Various methods of edge detection are known, and any method may be used in the present embodiment. Here, the first defect image ImgA is acquired one week before the acquisition of the defect image ImgB, so that edge detecting processing for the image ImgA may be performed at any timing after the acquisition of the image as long as the timing is before the edge detection for the image ImgB. However, an inspection recipe is preferably described in the recipe file so that the pattern inspection apparatus 10 may automatically perform the edge detecting processing immediately after the acquired image is stored in the database and the detection result may be saved in the database of the external hard disc drive MR2 as edge data. As a result, the time required for the defect inspection can be saved.

(Process in Step S4)

In the present embodiment, a difference vector is defined as a combination of corresponding points between the pattern edge of the defect image ImgA and the pattern edge of the defect image ImgB. While any method that is commonly used may be employed to search for the corresponding points of the pattern edges, the present embodiment employs a method that searches for the corresponding points on the basis of the distance between the corresponding points. This method will be described in more detail with reference to FIG. 5A to FIG. 5D. In accordance with the method shown in FIG. 5A to FIG. 5D, a correspondence is taken between an edge EA which is a portion of the pattern edge of the defect image ImgA and an edge EB which is a portion of the pattern edge of the defect image ImgB to find a difference vector.

First, as shown in FIG. 5A, sampling points SP are generated in the edge EA at regular intervals. Then, as shown in FIG. 5B, the edge EA is aligned (matched) with the edge EB. In order to improve the accuracy of the alignment, it is desirable to also carry out alignment in large regions. The edge EA and the edge EB in FIG. 5B are edges cut out of (unshown) greater pattern edges, respectively, for the sake of explanation.

Subsequently, as shown in FIG. 5C, searches for closest points on the edge EB to the sampling points SP are performed for all of the sampling points SP. A link between the sampling point SP to be the origin of the search and a point CP is referred to as a difference vector DV1. If the edge EA and the difference vector DV1 are only known, the edge EB is unnecessary in the subsequent processing. Particularly in patterns such as the patterns P1 and P2 shown in FIG. 3 and FIG. 4 in which most of the edges EA and EB correspond except in defective portions, a load on computer resources and the amount of data can be reduced by using the difference vector to describe the edge EB. The same basically applies to the compression of moving images. The difference vector DV1 generated in the example shown in FIG. 5C can be regarded as representing the change of the pattern P1 over one week. In the present embodiment, since a simple-shape defect generated in a reticle pattern having a relatively simple shape is given as an example, the difference vector is obtained by the above-mentioned simple method. However, it should be understood that any other method generally known may be used other than this method.

(Process in Step S5)

In the example shown in FIG. 3 and FIG. 4, the shape of the defect changes during one week. Therefore, this defect is a GD. The defect grows into a greater size along with repeated lot processing, and can become a defect that affects the yield of the device. Thus, such a situation need to be prevented by cleaning the reticle R before the defect grows as mentioned above. However, in order to minimize the cleaning cost, the cleaning has to be performed at an appropriate timing, as described above. Accordingly, in the present embodiment, the shape of the defect is predicted after elapse of an arbitrary period, e.g., one more week, and the influence on the yield is judged by the prediction result.

Figure 6:
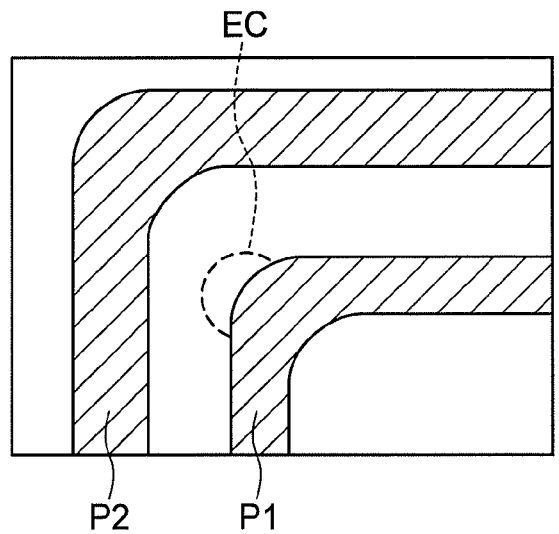
FIG. 6 is an explanatory diagram of step S5 in FIG. 2.

The defect shape after one more week (i.e., two weeks after the acquisition of the defect image ImgA) can be predicted by using the difference vector obtained in step S4 of FIG. 2. Thus, as shown in FIG. 5D, a difference vector DV2 having the same size and direction as the difference vector DV1 is then generated so as to originate from the point CP which is the corresponding point (the end point of the difference vector DV1) of the edge EB. Further, an edge EC is drawn by tracing the end points of the newly generated difference vectors DV2. This edge EC has the predicted shape of the defect after one more week. FIG. 6 shows an example in which the predicted shape is superposed on the SEM image. In this example, since the defect shape after two weeks is predicted, the same vector as the difference vector DV1 obtained from the edge EB before one week is used for the prediction. However, when, for example, the shape after two weeks is predicted, it can be obtained by doubling the length of the vector. On the other hand, when the shape after three days is predicted, it can be obtained by changing the length of the vector to $3/7$.

(Process in Step S6)

Figure 7:
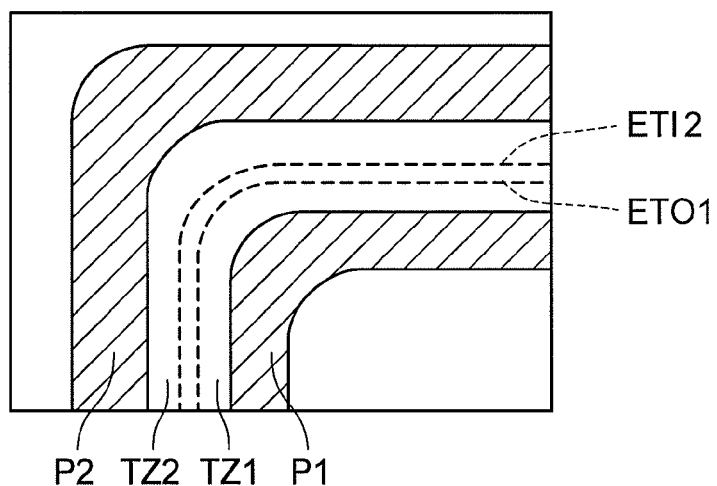
FIG. 7 is an explanatory diagram of step S6 in FIG. 2.

FIG. 7 shows portions of the shape specifications respectively found for the patterns P1 and P2 concerning the defects that affect the yield of the device. In FIG. 7, a sign TZ1 indicates the shape specification of the pattern P1, and a sign TZ2 indicates the shape specification of the pattern P2. A dotted line ETO1 indicates the outside borderline of the shape specification TZ1, and a dotted line ETI2 indicates the inside borderline of the shape specification TZ2.

A specific example of a method of creating the shape specifications TZ1 and TZ2 is described with reference to FIG. 8 to FIG. 13.

Figure 8:
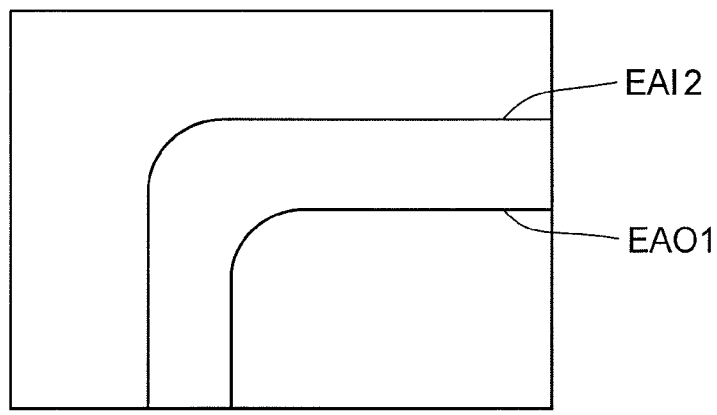
FIGS. 8 and 9 are explanatory diagrams of one example of a shape specification creating method.
Figure 9:
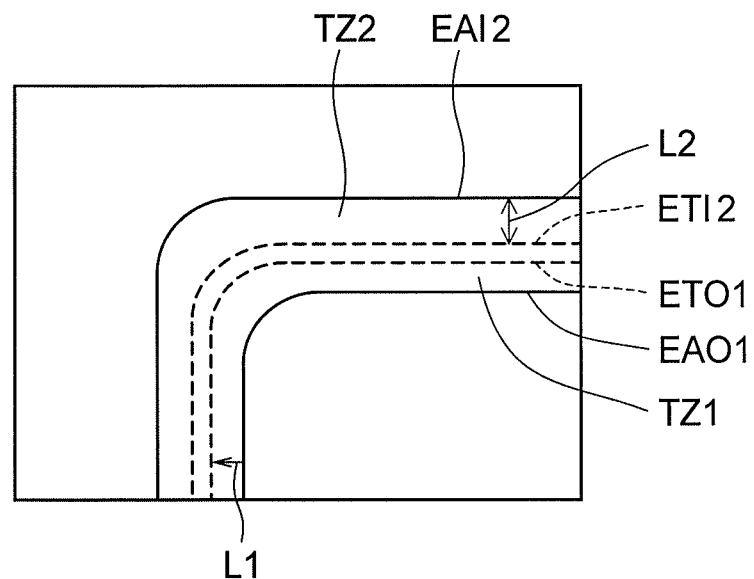

First, as allowable values of the shape judgment, a distance L1 is set for the pattern P1, and a distance L2 is set for the pattern P2. Further, as shown in FIG. 8 and FIG. 9, a set of all points separated by a distance L1 outward from an external edge EAO1 of the pattern P1 is prescribed as the outside borderline ETO1 of the shape specification TZ1. With regard to the pattern P2, a set of all points separated by a distance L2 inward from an internal edge EAI2 of the pattern P2 is prescribed as the inside borderline ETI2 of the shape specification TZ2 (FIG. 8 and FIG. 9). Although the border of the shape specification is here prescribed in a direction of higher risk, it is obvious that the borders of the shape specification may be prescribed on both the internal and external sides. Any method may be used to prescribe the shape specification instead of the method of designating these point sets as a boarder. For example, the shape specification may be prescribed by convolving a predefined unit pattern into the edge of a reference pattern.

Figure 10:
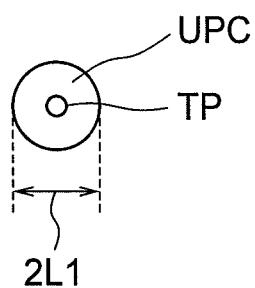
FIGS. 10 and 11 are explanatory diagrams of another shape specification creating method.
Figure 11:
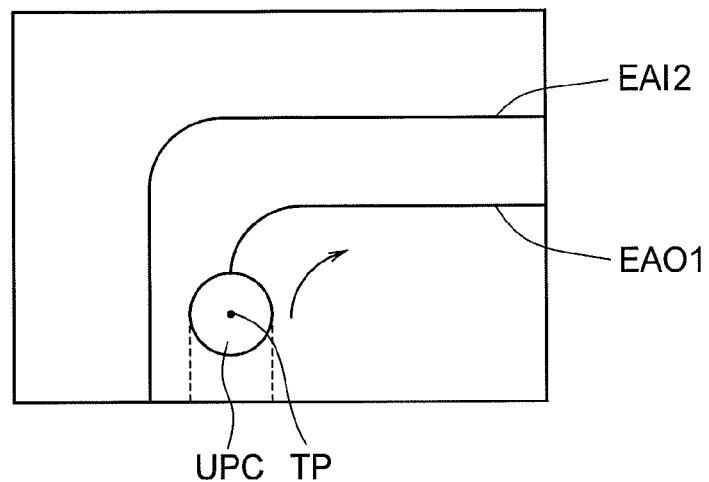
Figures 12A, 12B:
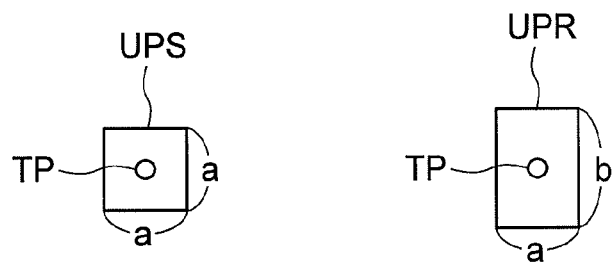
FIG. 12 is an explanatory diagram of still another shape specification creating method.

FIG. 10 shows one example of a unit pattern UPC comprising a perfect circle. The unit pattern UPC is not only provided with a radial length L1 but also provided with coordinates of a point TP which is a given point inside the circle and which intersects with the edge of the pattern. The value of a length 2L1 and a coordinate position of the point TP are allowable values. As shown in FIG. 11, the unit pattern UPC is aligned with the edge of the pattern P1 at the point TP so that the point TP may overlap the edge of the pattern P1. The unit pattern UPC is then moved along the edge of the pattern P1 so that the point TP may track the edge of the pattern P1. If the track of the edge of the unit pattern UPC drawn at this moment is recorded, a shape specification including a band-shaped region of the width 2L1 is generated. It should be understood that the shape of the unit pattern is not limited to the perfect circle and may be an elliptic shape or may be a square shape or rectangular shape, as shown in FIG. 12A and FIG. 12B. In this case, a shape specification having sharp corners is generated.

(Process in Step S7)

Figure 13:
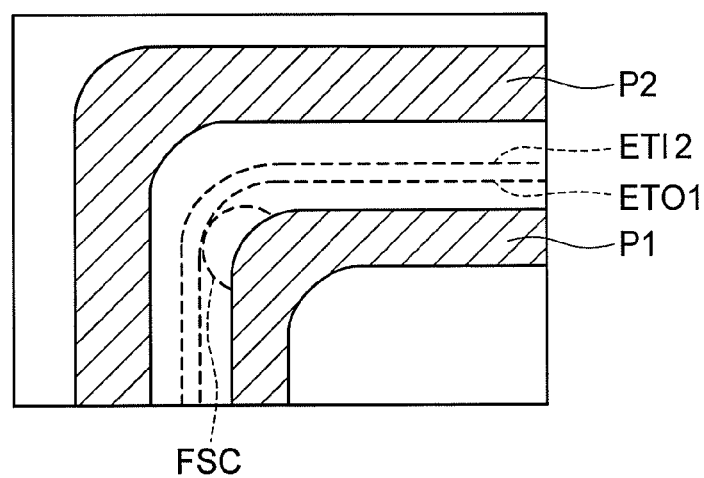
FIG. 13 is an explanatory diagram of step S7 in FIG. 2.

As shown in FIG. 13, a future defect shape is predicted for the shape specification (tolerance region) generated in step S6, and its inclusive relation is monitored so that the time at which the shape specification is not met can be predicted. To this end, a prediction shape may be obtained every other day and judged to find after how many days this shape fails to meet the specification for the first time. In the example shown in FIG. 13, a period when a predicted edge shape FSC overlaps the outside border ETO1 may be obtained. Thus, it is possible to predict when the GD starts affecting the yield. In the present embodiment, the external edge EAO1 of the pattern P1 and the internal edge EAI2 of the pattern P2 correspond to, for example, referential pattern edges, and the outside borderline ETO1 and the inside border ETI2 correspond to, for example, thresholds.

(Process in Step S8)

Finally, patterns are formed from the same reticle as usual until the predicted period comes. The reticle is cleaned or replaced before the predicted period comes. The semiconductor device is exposed by use of the cleaned reticle or a replacement reticle. Consequently, the semiconductor device can be manufactured at low costs and with a high yield.

Although the period when the GD starts affecting the yield is predicted in accordance with the time stamp of the obtained image in the case described above, the prediction is not limited to this. For example, the pattern forming apparatus 12 may count the number of processed lots and provide the counting result to the pattern inspection apparatus 10, and the pattern inspection apparatus 10 may predict the period in accordance with the total number of processed lots.

Moreover, in the embodiment described above, a defect generated on the reticle R is transferred on the wafer W by the pattern forming apparatus 12, and a pattern shape in the region of this defect is measured to carry out an inspection. However, transferring on the wafer is not essential. For example, the exposure optical system may be simulated by the computer to generate actual wafer images with respect to images of transmitted light and reflected light of the reticle. Defects may be detected in the wafer images to carry out an inspection in which the defect transferring tendency of the reticle is taken into account.

According to the embodiment described above, it is possible to carry out a low-frequency high-precision pattern inspection.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method for inspecting a pattern comprising:
    acquiring, by an imaging apparatus, a plurality of images of an inspection target pattern, the images having edges and being acquired at different acquisition times;
    detecting the edges;
    matching corresponding ones of the detected edges;
    obtaining differences between the matched edges to generate difference vectors;
    predicting an edge shape of the inspection target pattern at an arbitrary future time, based on:
        the difference vectors; and
        intervals between the acquisition times;
    setting a threshold corresponding to a required specification of the inspection target pattern; and
    predicting a future time at which the inspection target pattern will fail to meet the required specification, based on the predicted edge shape and the threshold.

2. The method of claim 1, further comprising:
    creating a tolerance region by use of a point separated from a referential pattern edge by an allowable value of the pattern,
    wherein the threshold is a border of the tolerance region, and
    the future time is predicted by determining an inclusive relation between the predicted edge shape and the tolerance region.

3. The method of claim 1, further comprising:
    counting a number of lots that have been processed to transfer the pattern to a substrate,
    wherein the future time is predicted by a total number of the processed lots.

4. The method of claim 1,
    wherein the pattern is formed on a reticle, and
    the inspection target pattern is a pattern transferred to a substrate by applying an energy ray to the reticle.

5. The method of claim 4, further comprising:
    detecting defects over an entire surface of the reticle; and
    sampling at least one of the detected defects,
    wherein the inspection target pattern is imaged with reference to coordinates of the sampled defect.

6. The method of claim 5,
    wherein the sampling is performed based on sizes of the defects.

7. The method of claim 5,
    wherein the sampling is performed based on an order of risk of the defects.

8. The method of claim 5,
    wherein the sampling is performed by weighting in which sizes of the defects and an order of risk of the defects are taken into account.

9. The method of claim 5,
    wherein the pattern is a two-dimensional pattern.

10. A semiconductor device manufacturing method comprising:
    acquiring, by an imaging apparatus, a plurality of images of an inspection target pattern, the images having edges and being acquired at different acquisition times, the inspection target pattern being a pattern transferred from a reticle to a substrate by applying an energy ray to the reticle;
    detecting the edges;
    matching corresponding ones of the detected edges;
    obtaining differences between the matched edges to generate difference vectors;
    predicting an edge shape of the inspection target pattern at an arbitrary future time, based on:
        the difference vectors; and
        intervals between the acquisition times;
    setting a threshold corresponding to a required specification of the inspection target pattern;
    predicting a future time at which the inspection target pattern will fail to meet the required specification, based on the predicted edge shape and the threshold; and
    cleaning or replacing the reticle before arrival of the predicted future time.

11. The method of claim 10, further comprising:
    detecting defects over an entire surface of the reticle; and
    sampling at least one of the detected defects,
    wherein the inspection target pattern is imaged with reference to coordinates of the sampled defect.

12. The method of claim 11,
    wherein the sampling is performed based on sizes of the defects.

13. The method of claim 11,
wherein the sampling is performed based on an order of risk of the defects.

14. The method of claim 11,
wherein the sampling is performed by weighting in which sizes of the defects and an order of risk of the defects are taken into account.

15. The method of claim 11,
wherein the pattern is a two-dimensional pattern.

* * * * *